United States Patent [19]

Straub

[11] Patent Number: 5,244,887
[45] Date of Patent: Sep. 14, 1993

[54] STANOLS TO REDUCE CHOLESTEROL ABSORPTION FROM FOODS AND METHODS OF PREPARATION AND USE THEREOF

[76] Inventor: Carl D. Straub, 13700 Rivercrest Dr., Little Rock, Ark. 72212

[21] Appl. No.: 835,590

[22] Filed: Feb. 14, 1992

[51] Int. Cl.$^5$ .............................................. A61K 31/56
[52] U.S. Cl. ..................................... 514/182; 426/541
[58] Field of Search ......................... 514/182; 426/541

[56] References Cited

U.S. PATENT DOCUMENTS

| | | |
|---|---|---|
| 3,085,939 | 4/1963 | Wruble et al. |
| 3,203,862 | 8/1965 | Jones |
| 3,495,011 | 2/1970 | Fossel |
| 3,689,663 | 9/1972 | Krämer et al. |
| 3,751,569 | 8/1973 | Erickson |
| 3,849,554 | 11/1974 | Wintz |
| 3,865,939 | 2/1975 | Jandacek |
| 3,881,005 | 4/1975 | Thakkar et al. |
| 3,954,976 | 5/1976 | Mattson et al. |
| 3,959,492 | 5/1976 | Coulston et al. |
| 4,034,083 | 8/1977 | Mattson |
| 4,117,121 | 9/1978 | Gallo-Torres |
| 4,195,084 | 3/1980 | Ong |
| 4,242,502 | 12/1980 | Malinow et al. |
| 4,351,844 | 9/1982 | Patchett et al. |
| 4,420,427 | 12/1983 | Hamunen |
| 4,427,668 | 1/1984 | Javitt |
| 4,602,003 | 7/1986 | Malinow |
| 4,603,142 | 7/1986 | Burger et al. |
| 4,680,290 | 7/1987 | Cassal |
| 4,789,664 | 12/1988 | Seligson |
| 4,789,670 | 12/1988 | Tipton et al. |
| 4,789,682 | 4/1988 | Stokker |
| 4,824,672 | 4/1989 | Day et al. |
| 4,849,222 | 6/1989 | Broaddus |
| 4,883,788 | 11/1989 | Day et al. |
| 4,900,726 | 2/1990 | Tipton et al. |
| 4,950,140 | 8/1990 | Pflaumer et al. |

OTHER PUBLICATIONS

"Lowering Blood Cholesterol to Prevent Heart Disease." Consensus Development Conference on Lowering Blood Cholesterol to Prevent-Heart Disease (NIH) J. Am. Med. Assoc. 253, 2080–2086 (1985).

National Heart Lung and Blood Institute. Report of the National Cholesterol Education Program: Expert Panel on Detection. "Evaluation and Treatment of High Blood Cholesterol Levels in Adults." Arch. Int. Med. 148, 36–39 (1988).

"Successful Prevention of Experimental Hypercholesterolemia and Cholesterol Atheroschlerosis in the Rabbit." Pollak, O. J. Circulation 7, 696–701 (1953).

"The Effect of Beta Sitosterol in the Serum Lipids of Young Men with Arteriosclerotic Heart Disease." Farquhar, J. W. Smith, R. E., and Dempsey, M. E. Circulation 14, 77–82 (1956).

"Effects of Plant Sterols on Cholesterol Metabolism in Man." Kudchodkar, B. J., Horlick, L., and Sodhi, H. S. Atherosclerosis 23, 239–248 (1976).

"Plant Sterols as Cholesterol-Lowering Agents: Clinical Trials in Patients with Hypercholesterolemia and Studies of Sterol Balance", Lees, A. M., Mok, H. Y. I., Lees, R. S., McCluskey, M. A. and Grundy S. M. Atherosclerosis 28, 325–388 (1977).

"Response of Serum Lipids and Lipoproteins of Man to beta-sitosterol and Safflower Oil. A Long Term Study." J. W. and Sokolow, M. Circulation 17, 890–899 (1958).

"Dietary Plant Sterols: Current status in human and animal sterol metabolism." Subbisah, M. T. Ravi, Am.

"Effect of Low-Dose Sitostanol on Serum Cholesterol in Patients with Hypercholesterolemia." Heinemann, T., Leiss, O. and von Vergmann, K. Atheroschlerosis, 61, 219–233 (1986).

"Comparison of Sitosterol and Sitostanol on Inhibition of Intestinal Cholesterol Absorption." Heinemann, T., Pietruck, B. Kullak-Ubilick, G. and von Bergmann, K. 4th Cologne Atherosclerosis Conference 1988. Birkhauser Verlag, Basel p. 117.

"Comparison of Absorption and Metabolism of $\beta$-Sitosterol and $\beta$-Sitostanol in Rats." Ikeda, I and Sugano M. Atherosclerosis 30, 227–237 (1978).

"Some Aspects of Mechanisms of Inhibition of Cholesterol Absorption of $\beta$-Sitostersol". Ikeda, I. and Sugano, M. Biochem. Biophys. Acta 732, 651–658 (1983).

"Optimizing the Effect of Plant Sterols on Cholesterol Absorption in Man." Mattson, F. H., Grundy, S. M., and Crouse, J. R. Am. J. Clin. Nutr. 35, 697–700 (1982).

"Effect of Plant Sterols on Serum Lipids and Atherosclerosis." Pollack, O. J. Pharmac. Ther. 31, 177–208 (1985).

*The Lipids.* vol. 1, Deuel, H. J. Jr. Interscience Publishers, 1951, New York, pp. 348–361.

Primary Examiner—Marianne M. Cintins
Assistant Examiner—Rebecca Cook
Attorney, Agent, or Firm—Staas & Halsey

[57] ABSTRACT

Food additives containing stanols and methods for making and using the food additives. These food additives are intended to reduce cholesterol absorption from foods and beverages which contain cholesterol, e.g., meat, eggs, and dairy products. Specific stanols include sitostanol, clionastanol, 22,23 dihydrobrassicastanol, campestanol, and mixtures thereof.

5 Claims, No Drawings

STANOLS TO REDUCE CHOLESTEROL ABSORPTION FROM FOODS AND METHODS OF PREPARATION AND USE THEREOF

BACKGROUND OF THE INVENTION

This invention relates to reducing cholesterol absorption from foods. Specifically, this invention provides a plant stanol food additive for reducing the absorption of cholesterol, a method of preparation, and a method of use of such a food additive.

Cholesterol has been known for many years to be a component of atherosclerotic plaques. Mounting evidence indicates diets high in cholesterol usually increase the levels of cholesterol in the blood which, in turn, increase risk of atherosclerotic disease with its attendant manifestations of heart attack, stroke and other tissue injuries resulting from atherosclerosis. Cholesterol absorbed from dietary sources is therefore thought to increase risk of atherosclerotic disease.

Based on a vast body of scientific evidence the National Institutes of Health (NIH) issued the following consensus statement which identified the risk factors for heart disease: "Lowering Blood Cholesterol to Prevent Heart Disease—Consensus Development Conference on Lowering Blood Cholesterol to Prevent Heart Disease", J. Am. Med. Assoc., 253, 2080–2086 (1985). NIH put forth a public warning against the consumption of foods with high cholesterol content. This recommendation, along with previous like statements by medical scientists and subsequent reinforcement in National Heart Lung and Blood Institute's "Report of the National Cholesterol Education Program, Expert Panel on Detection, Evaluation of Treatment of High Blood Cholesterol Levels in Adults", Arch. Int. Med. 148, 36–69 (1988), has led to a decrease in per capita consumption in the United States of high-cholesterol foods, especially meat and dairy products.

Other than avoidance or reduced consumption of high cholesterol foods, measures available without prescription to the general public to reduce the absorption of cholesterol from the diet have met with little success. Intake of dietary fibers for reducing cholesterol absorption requires large percentages of bulk fiber to be effective. For example, psyllium is required at from 5% to 30% by weight in cookies (U.S. Pat. No. 4,950,140, Pflaumer et al.). A formation of guar gum and calcium carbonate for therapeutic purposes to lower blood cholesterol requires 5 grams at each mealtime to be effective (U.S. Pat. No. 4,883,788, Day et al.).

The use of $\beta$-sitosterol, a plant sterol, to reduce blood cholesterol has been known for a number of years. In 1953 Pollak reported the prevention of experimental atherosclerosis in rabbits by feeding a 6 to 1 ratio of sitosterol to cholesterol in feed. "Successful Prevention of Experimental Hypercholesterolemia and Cholesterol Atherosclerosis in the Rabbit", Pollak, O. J. Circulation, 7, 696–701 (1953). In 1956, Farquhar et al. reported significant reduction (17%) of serum cholesterol in young men with atherosclerotic heart disease. The dosage was 12–18 grams per day given in divided doses at mealtimes. "The Effect of Beta Sitosterol in Serum Lipids of Young Men with Arteriosclerotic Heart Disease", Farquhar, J. W., Smith, R. E., and Dempsey, M. E., Circulation 14 77–82 (1956).

Eli Lily marketed a sterol preparation from soybean oil, and later, from tall oil, called Cytellin ®. In doses of 3 grams t.i.d. the soybean-derived Cytellin ® lowered blood cholesterol by about 9% according to one report. "Effects of Plant Sterols on Cholesterol Metabolism in Man", Kucchodkar, B. J., Horlick, L., and Sodhi, H. S., Atherosclerosis, 23, 239–248 (1976). The tall oil-derived Cytellin ® which was 93% $\beta$-sitosterol, required dosages of from 3 to 18 grams per day to lower blood cholesterol by about 12%. "Plant Sterols as Cholesterol-Lowering Agents: Clinical Trials in Patients with Hypercholesterolemia and Studies of Sterol Balance", Lees, A. M., Mok, H. Y. I., Lees, R. S., McCluskey, M. A. and Grundy, S. M., Atherosclerosis, 28, 325–33 (1977). Other studies have substantiated the cholesterol lowering effect of sterols. "Response of Serum Lipids and Liproteins of Man to beta-sitosterol and Safflower Oil, A Long Term Study", Farquhar, J. W. and Sokolow, M., Circulation, 17, 890–899 (1958); and "Dietary Plant Sterols—Current Status in Human and Animal Sterol Metabolism", Subbisah, M. T. Ravi, Am. J. Clin. Nutr., 26, 219–225 (1973).

Thus, it is accepted that sterols in dosages of 3–18 grams per day can lower absorption of cholesterol from the gastro-intestinal tract and thereby reduce blood cholesterol.

In most of the above-mentioned studies the use of plant sterols is designed for the therapeutic use of lowering blood cholesterol in patients who have abnormally high blood cholesterol and are in need of treatment. Other preparations used for therapeutic effect include modified sterol molecules. See U.S. Pat. Nos. 4,602,003, Malinow, and 4,242,502, Malinow et al., which teach the synthesis and therapeutic use of saponins which are closely related to sterols. See also U.S. Pat. No. 4,117,121; Gallo-Jones, which discloses synthesis and use of another group of compounds which is closely related to sterols, $3\alpha$, $12\alpha$ dihydro cholanes, as therapeutic agents for lowering blood cholesterol levels.

Other research has demonstrated that stanols, the $5\alpha$ saturated derivatives of plant sterols, are more effective as therapeutic agents in lowering blood cholesterol on a weight for weight basis than sterols. "Effect of Low-Dose Sitostanol on Serum Cholesterol in Patients with Hypercholesterole mia", Heinemann, T., Leiss, O. and von Bergamann, K., Atherosclerosis, 61, 219–223 (1986). This study demonstrated that 1.5 grams per day of a stanol mixture derived from soybean sterols was effective in lowering blood cholesterol by 15% after four weeks of therapy in patients with hypercholesterolemia, and suggested that low-dose sitostanol might be useful in therapy for patients afflicted with mild hypercholesterolemia.

In a comparison between sterols and stanols, equal amounts of sitostanol and sitosterol were infused into the gastro-intestinal (G.I.) tracts of human volunteers. Infusion of sterols resulted in a 50% reduction of cholesterol absorption while stanol infusion resulted in an 85% reduction in cholesterol absorption. "Comparison of Sitosterol and Sitostanol on Inhibition of Intestinal Cholesterol Absorption", Heinemann, T., Pietruck, B., Kullak-Ubilick, G., and von Bergmann, K., 4th Cologne Atherosclerosis Conference 1988, Birkhauser Verlag, Basel P. 117. The authors also measured absorption of the sterols and stanols. They found that there was a small but significant amount of sitosterol absorbed from the G.I. tract, but there was no measurable absorption of sitostanol under identical experimental conditions. These conclusions were verified by feeding studies of the two compounds in rats. "Comparison of Absorption and Metabolism of β-Sitosterol and β-Sitostanol in Rats", Ikeda I. and Sugano M., Atherosclerosis, 30, 227-237 (1978).

Stanols are more stable in heat and air than sterols because there are no unsaturated carbon-carbon bonds in stanols (U.S. Pat. No. 4,789,670, Tipton et al.).

Thus, stanols have three advantages over sterols for the inhibition of cholesterol absorption from the G.I. First, stanols are more effective by weight than sterols; second, stanols are absorbed from the G.I. tract to a lesser extent than sterols; and third, stanols are more chemically stable than sterols.

Stanols, in the above-mentioned report by Heinemann et al., are suggested as therapeutic agents directed toward treatment of mild hypercholesterolemia in specific patients in need of treatment. The instant invention is not intended for therapeutic purposes, but rather for use by the general public. The methods and composition of the instant invention comprise a food additive. Furthermore, the instant invention is intended for use in decreasing cholesterol absorption from only the food to which it is added.

Several compositions have been studied as food additives for the purpose of reducing cholesterol absorption from food products; they are described in contrast to the above-mentioned therapeutic which are used for lowering blood cholesterol level A food product including sucrose polyesters and vegetable proteins as a substitute for foods high in cholesterol such as beef is disclosed in U.S. Pat. Nos. 4,789,664, Tipton et al. 4,034,083, Mattson, discloses a fat substitute including polyol fatty acid esters fortified with fat soluble vitamins as a method of reducing cholesterol absorption when used as a salad oil or cooking oil. "Optimizing the Effect of Plant Sterols on Cholesterol Absorption in Man", Mattson, F. H., Grundy, S. M., and Crouse, J. R., Am. J. Clin. Nutr. 35, 697–700 (1982) suggested the inclusion of sterols for food additives as well as for therapeutic agents. "Effect of Plant Sterols on Lipids and Atherosclerosis", Pollack, O. J., Pharmac. Ther., 31, 177-208 (1985) suggested the inclusion plant sterols such as β-sitosterol in such foods as butter and margarine to "counteract not only the cholesterol in butter but all other dietary cholesterol and cholesterol from non-dietary sources available for absorption and re-absorption." In another study the ratio of about 2:1 (weight:weight) sterol to cholesterol was required to effect a 50% reduction in cholesterol absorption (e.g., from scrambled eggs), Mattson et al., supra (1982). Several patents also disclose uses of sterols in edible cooking oils for hypocholesterolemic effect (U.S. Pat. Nos. 3,865,939, Jandacek; 3,751,659, Erickson; and 3,085,939, Wruble et al.).

Conspicuously lacking in the above-identified literature is a food additive composition for reducing cholesterol absorption which is inexpensive, stable in storage, non-absorbable, and effective in small amounts to make it convenient for use.

Moreover, at this time the only widespread and safe method of reducing absorption of cholesterol from food products is actual avoidance of foods which contain cholesterol such as meats, eggs, and dairy products, thereby making maintenance of nutritious diets less convenient since meat, eggs, and dairy products are excellent sources of nutrition and staple foods of popular diets in many countries.

Furthermore, most pharmaceutical agents presently available for lowering blood cholesterol are relatively expensive and have side effects.

SUMMARY OF THE INVENTION

Accordingly, it is a purpose of this invention to provide a food additive and method for reducing cholesterol absorption from foods.

Another purpose of this invention is to take full advantage of the excellent nutritional value of meat, eggs, and dairy products by re-establishing their inclusion in the popular diet, thereby aiding the maintenance of nutritious diets.

Still another purpose of the instant invention is to provide an inexpensive, non-absorbable, and stable food additive composition for reducing cholesterol absorption from food.

Yet another purpose of the present invention is to provide a method of reducing cholesterol absorption without introducing any side effects.

Still another purpose of the invention is to provide a food additive to reduce cholesterol absorption which is effective in relatively small amounts making it convenient for use.

To achieve the foregoing and other purposes of the present invention there are provided novel uses of compounds which are inhibitors of cholesterol absorption. The compounds are plant stanols, particularly β-sitostanol, clionastanol, 22,23, dihydrobrassicastanol, campestanol, and mixtures thereof. Said plant stanols may be used with or without suitable carriers, dispersants, and anti oxidants. The food additive composition of the invention can be added before, during, or after cooking, and is especially intended to be used by the general public as an additive for food products which contain cholesterol, especially meat, egg and dairy products.

DESCRIPTION OF THE PREFERRED EMBODIMENTS

This invention relates to novel uses of plant stanols as food additives. The term stanols used herein refers to plant sterol derivatives in which all carbon-carbon bonds in the rings are saturated. The principal stanols of the instant invention are those which are composed of 28 or 29 carbon atoms. Four major plant stanols are campestanol, 22,23 dihydrobrassicastanol, β-sitostanol, and clionastanol. *The Lipids*, Vol. 1, Deuel, H. J., Jr., Interscience Publishers, 1951, N.Y., pp. 348–361. These four stanols have the following structure.

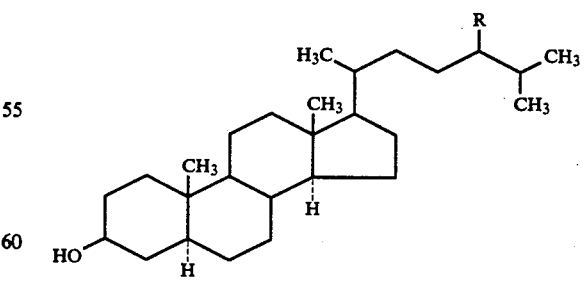

where R=CH$_3$ for campestanol and its epimer, 22,23 dihydrobrassicastanol and where R=C$_2$H$_5$ for sitostanol and its epimer, clionastanol. The C$_{28}$ stanols campestanol and 22,23 dihydrobrassicastanol differ only by their steric configuration at C$_{24}$. The C$_{29}$ stanols, likewise, differ only by the steric configuration at C$_{24}$.

Alternate nomenclature for clionastanol is (3β, 5α, 24S)-Stigmast-5an-3-ol; sitostanol is (3β, 5α 24R)-Stigmast-5an-3-ol; campestanol is (3β, 5α, 24R)-Ergost-5an-3-ol; 22,23 dihydrobrassicastanol is (3β, 5α, 24S)-Ergost-5an-3-01.

While stanols are found in small amounts in nature, they can easily be made from the much more abundant plant sterols by hydrogenation.

Plant sterols, precursors of stanols, can be obtained from vegetable oils, vegetable oil sludge, vegetable oil distillates, and other plant oil sources such as tall oils by relatively simple and inexpensive means. For example, a preparation of sterols from vegetable oil sludge by using solvents such as methanol is taught in U.S. Pat. No. 4,420,427, Hamunen. Stanols, a primary component of the instant invention, can be prepared by hydrogenating sterols by any of several methods known to those skilled in the art. Since the sterols prepared from plant sources are usually mixtures of several different sterols, hydrogenation leads to a mixture of several different stanols. Sterols, which differ only by the degree of unsaturation in the carbon bonds of the ring or side chains, upon hydrogenation usually produce stanols which differ only in epimeric centers such as the $C_{24}$ carbon.

As an example, a hydrogenation product of sterols obtained by Heinemann et al., supra (1986) from soybean oil is reported to contain 91% stanols (88% sitostanol and 3.3% campestanol) and 8.7 residual sterols (campesterol). As seen in this report, a hydrogenation process may leave some residual sterols unreacted. Residual sterols of minor proportion, preferably less than 10%, are acceptable for the compositions and methods of the instant invention.

Pure specific sterol preparations can be hydrogenated as well, with the production of pure stanols which can be utilized in the instant invention.

While stanols are found in relatively small quantities as naturally occurring components of many plants, they exist in such small percentages compared to other plant components that they are not cost effective to extract separately. However, significant quantities of stanols may be easily and inexpensively made from more abundant sterols through hydrogenation.

Although not wishing to be bound by any theoretical explanation of the invention, it is believed that the mechanism by which the sterols, and presumably the stanols, act is the impairment of micellar solubility of cholesterol in the lumen intestine. "Some Aspects of Mechanisms of Inhibition of Cholesterol Absorption of β-Sitosterol", Ikeda, I. and Sugano, M. Biochem. Biophys. Acta, 732, 651–658 (1983). Stanols are more effective by weight than sterols in therapeutic applications by factors of from 2–10 (compare Heinemann, supra, 1986 with Lees, supra, 1977).

Desirable characteristics of a food additive composition for reducing cholesterol absorption include absence of side effects, efficacy without absorption of the compound, stability at cooking temperatures, stability in storage and in oxidizing environments, low cost, availability, and small dose requirements. The only known compositions which satisfy some of the above desirable characteristics are those in which plant sterols are the primary component. However, the advantages of the instant invention over such plant sterol compositions include:

a) effective in lesser amounts than sterols,
b) absorbed less from the G.I. tract than sterols, and
c) more stable than sterols in storage and in oxidizing environments.

Although the composition of the invention may be used in various embodiments it may be said, in general, that greatest effectiveness is obtained when the stanols are evenly distributed in finely divided form throughout the food product or beverage to which it is added. This can be accomplished by dissolution of the stanols or by suspension of the stanols in an emulsion.

Stanols can be dissolved in a solubilizing agent such as vegetable oil, monoglycerides, diglycerides, triglycerides, tocopherols, the like, and mixtures thereof.

Effective carriers for making suspensions or emulsions of stanols include water, alcohols, polyols, other edible compounds in which the stanols are partially soluble or not soluble, and mixtures thereof. Such suspensions are aided by dispersing agents such as lecithin, other phospholipids, sodium lauryl sulfate, fatty acids, salts of fatty acids, fatty acid esters, other detergent-like molecules and mixtures thereof. The purpose of the dispersing agent is to aid formation of an emulsion in which the stanols are uniformly dispersed.

The food additive composition can further include an antioxidant such as, ascorbic acid, tocopherols, inexpensive synthetic antioxidants, and mixtures thereof. The preferred antioxidant for the instant invention is tocopherols. Tocopherols will not interfere with the solubility of the stanols in the vegetable oil, but, in fact, are effective solubilizing agents themselves for stanols.

A preferred food additive composition of the instant invention comprises (a) about 74.8% vegetable oil, (b) about 1.2% tocopherols, and (c) about 25% stanols. Thus, the resulting composition of vegetable oil, stanols, and tocopherols has three desirable attributes each of which compliment the food additive:

a. stanols remain in solution or uniformly suspended in the food additive composition,
b. absorption of cholesterol from the G.I. tract is reduced by stanols;
c. foods and beverages are protected from oxidation by the tocopherols.

Another aspect of this invention relates to the use of the novel food additive composition described hereinbefore.

The method by which the novel food additive composition is used to reduce cholesterol absorption from foods and beverages includes the step of comingling the food additive composition with foods and beverages, mixing until uniformly blended. In a preferred method of commingling the indicated food additive with foods and beverages which contain cholesterol, the food additive is added such that the amount of stanols in the food additive is in the ratio of about 1:1 by weight to the cholesterol contained in the foods and beverages. Thus, for a food additive composition which comprises 25% stanols and a food which contains about 0.1% cholesterol (such as hamburger), the ratio of food additive to food product is about 1:250 by weight.

The food additive composition of the invention can be commingled with foods by a step selected from the group of infusion, injection, mixing, kneading, blending, immersion, spraying, surface application (for example, brushing and basting), cooking in oils which contain the food additive-invention, and combinations thereof. Preferred steps for commingling the food additive-invention with ground meat are kneading and mixing; for meat pieces such as steaks, chicken breasts, and chopped, diced or sliced meat, the preferred steps are injection, infusion, spraying, immersion, and surface applications such as basting and marinating. Two preferred steps for comingling the food additive-invention with beverages are mixing and blending.

The stanols can be added alone to foods or added with suitable carriers such as triglycerides, monoglycerides, fatty acid, fatty acid esters, alcohols, polyols and vegetable oils.

The stanols can be added with dispersants alone or in combination with the carriers. Examples of suitable dispersants are lecithin, polysorbate 80, sodium lauryl sulfate, and the like.

The compounds of the invention will be used as food additives to foods such as meats, eggs and dairy products.

The foregoing is considered illustrative only of the principles of the invention. Further, since numerous modifications and changes will readily occur to those skilled in the art, it is not desired to limit the invention to the exact construction and operation shown and described. Accordingly, all suitable modifications and equivalents may be resorted to that fall within the scope of the invention and the appended claims.

What is claimed is:

1. A method for making a food additive composition, comprising the step of:
   dissolving a stanol selected from the group consisting of clionastanol, 22,23 dihydrobrassicastanol, campestanol, sitostanol, and mixtures thereof, with an edible solubilizing agent, an effective amount of a suitable antioxidant and an effective amount of a suitable dispersant.

2. The method of claim 1, wherein:
   the edible solubilizing agent is selected from the group consisting of triglycerides, vegetable oils, tocopherols, alcohols, and polyols.

3. The method of claim 1, wherein:
   the antioxidant is selected from the group consisting of tocopherols.

4. The method for making a food additive composition comprising the step of:
   homogenizing a stanol selected from the group consisting of clionastanol, 22,23 dihydrobrassicastanol, campestanol, sitostanol, and mixtures thereof, with an effective amount of a suitable dispersant and an effective amount of a suitable antioxidant in a carrier.

5. The method of claim 4, wherein:
   the antioxidant is selected from the group consisting of tocopherols.

* * * * *